(12) United States Patent  
Takamizawa

(10) Patent No.: US 7,612,350 B2  
(45) Date of Patent: Nov. 3, 2009

(54) SCANNING MICROSCOPE AND SPECIMEN IMAGE OBTAINING METHOD IN WHICH ADJACENT DATA OBTAINING POINTS ARE NOT CONSECUTIVELY OBTAINED

(75) Inventor: Nobuhiro Takamizawa, Sagamihara (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/330,429

(22) Filed: Jan. 12, 2006

(65) Prior Publication Data

US 2006/0157638 A1 Jul. 20, 2006

(30) Foreign Application Priority Data

Jan. 18, 2005 (JP) ............................. 2005-010841

(51) Int. Cl.  
*G01N 21/64* (2006.01)

(52) U.S. Cl. ................................... 250/461.2; 356/318

(58) Field of Classification Search ............ 250/458.1, 250/459.1, 205, 461.2, 201.3; 356/318  
See application file for complete search history.

(56) References Cited

U.S. PATENT DOCUMENTS

| | | | |
|---|---|---|---|
| 4,786,170 A | 11/1988 | Groebler | |
| 5,028,802 A | 7/1991 | Webb et al. | |
| 6,437,910 B1 * | 8/2002 | Watanabe | 359/368 |
| 6,510,237 B1 * | 1/2003 | Peltie et al. | 382/128 |
| 6,646,271 B2 * | 11/2003 | Yokokawa et al. | 250/458.1 |
| 7,323,679 B2 | 1/2008 | Wolleschensky et al. | |
| 2002/0121611 A1 | 9/2002 | Yokokawa et al. | |
| 2002/0160369 A1 | 10/2002 | Dorsel et al. | |
| 2003/0035109 A1 | 2/2003 | Hartwich et al. | |
| 2004/0232351 A1 * | 11/2004 | Ishiura et al. | 250/461.2 |
| 2006/0011859 A1 | 1/2006 | Wolleschensky et al. | |
| 2007/0132998 A1 * | 6/2007 | Tang et al. | 356/417 |
| 2008/0149818 A1 | 6/2008 | Wolleschensky et al. | |

FOREIGN PATENT DOCUMENTS

| | | | |
|---|---|---|---|
| EP | 1209461 A1 | 5/2002 |
| EP | 1 617 254 A1 | 1/2006 |
| GB | 2 416 442 A | 1/2006 |
| JP | 10-010436 A | 1/1998 |

OTHER PUBLICATIONS

English language Summons to Attend Oral Proceedings dated Nov. 7, 2008, issued in a counterpart European Application.

* cited by examiner

*Primary Examiner*—Georgia Y Epps  
*Assistant Examiner*—Kevin Wyatt  
(74) *Attorney, Agent, or Firm*—Frishauf, Holtz, Goodman & Chick, P.C.

(57) ABSTRACT

A scanning microscope includes a light source unit that projects laser light, an optical system that converges and applies the laser light onto data obtaining points on a specimen, and a data obtaining order deciding unit that decides a data obtaining order such that adjacent data obtaining points are not consecutive in the data obtaining order. A scanning unit scans the laser light in accordance with the data obtaining order, a detector detects detection light from the data obtaining points, respectively, and a storage unit stores luminance information on the detection light detected by the detector in association with positional information on the data obtaining points, respectively. An image formation unit forms a two-dimensional image based on the stored associated luminance and positional information.

16 Claims, 6 Drawing Sheets

FIG. 9

|   | A |   |   |   | B |   |   |   | C |   |   |   | D |   |   |   |
|---|---|---|---|---|---|---|---|---|---|---|---|---|---|---|---|---|
|   | 1 | 9 | 17 | 25 | 5 | 13 | 21 | 29 | 2 | 10 | 18 | 26 | 6 | 14 | 22 | 30 |
|   | 33 | 41 | 49 | 57 | 37 | 45 | 53 | 61 | 34 | 42 | 50 | 58 | 38 | 46 | 54 | 62 |
|   | 65 | 73 | 81 | 89 | 69 | 77 | 85 | 93 | 66 | 74 | 82 | 90 | 70 | 78 | 86 | 94 |
|   | 97 | 105 | 113 | 121 | 101 | 109 | 117 | 125 | 98 | 106 | 114 | 122 | 102 | 110 | 118 | 126 |
|   | 129 | 137 | 145 | 153 | 133 | 141 | 149 | 157 | 130 | 138 | 146 | 154 | 134 | 142 | 150 | 158 |
|   | 161 | 169 | 177 | 185 | 165 | 173 | 181 | 189 | 162 | 170 | 178 | 186 | 166 | 174 | 182 | 190 |
|   | 193 | 201 | 209 | 217 | 197 | 205 | 213 | 221 | 194 | 202 | 210 | 218 | 198 | 206 | 214 | 222 |
|   | 225 | 233 | 241 | 249 | 229 | 237 | 245 | 253 | 226 | 234 | 242 | 250 | 230 | 238 | 246 | 254 |
|   | 3 | 11 | 19 | 27 | 7 | 15 | 23 | 31 | 4 | 12 | 20 | 28 | 8 | 16 | 24 | 32 |
|   | 35 | 43 | 51 | 59 | 39 | 47 | 55 | 63 | 36 | 44 | 52 | 60 | 40 | 48 | 56 | 64 |
|   | 67 | 75 | 83 | 91 | 71 | 79 | 87 | 95 | 68 | 76 | 84 | 92 | 72 | 80 | 88 | 96 |
|   | 99 | 107 | 115 | 123 | 103 | 111 | 119 | 127 | 100 | 108 | 116 | 124 | 104 | 112 | 120 | 128 |
|   | 131 | 139 | 147 | 155 | 135 | 143 | 151 | 159 | 132 | 140 | 148 | 156 | 136 | 144 | 152 | 160 |
|   | 163 | 171 | 179 | 187 | 167 | 175 | 183 | 191 | 164 | 172 | 180 | 188 | 168 | 176 | 184 | 192 |
|   | 195 | 203 | 211 | 219 | 199 | 207 | 215 | 223 | 196 | 204 | 212 | 220 | 200 | 208 | 216 | 224 |
|   | 227 | 235 | 243 | 251 | 231 | 239 | 247 | 255 | 228 | 236 | 244 | 252 | 232 | 240 | 248 | 256 |
|   | E |   |   |   | F |   |   |   | G |   |   |   | H |   |   |   |

FIG. 10

|   | A |   |   |   |   |   |   |   | B |   |   |   |   |   |   |   |
|---|---|---|---|---|---|---|---|---|---|---|---|---|---|---|---|---|
|   | 1 | 5 | 9 | 13 | 17 | 21 | 25 | 29 | 2 | 6 | 10 | 14 | 18 | 22 | 26 | 30 |
|   | 33 | 37 | 41 | 45 | 49 | 53 | 57 | 61 | 34 | 38 | 42 | 46 | 50 | 54 | 58 | 62 |
|   | 65 | 69 | 73 | 77 | 81 | 85 | 89 | 93 | 66 | 70 | 74 | 78 | 82 | 86 | 90 | 94 |
|   | 97 | 101 | 105 | 109 | 113 | 117 | 121 | 125 | 98 | 102 | 106 | 110 | 114 | 118 | 122 | 126 |
|   | 129 | 133 | 137 | 141 | 145 | 149 | 153 | 157 | 130 | 134 | 138 | 142 | 146 | 150 | 154 | 158 |
|   | 161 | 165 | 169 | 173 | 177 | 181 | 185 | 189 | 162 | 166 | 170 | 174 | 178 | 182 | 186 | 190 |
|   | 193 | 197 | 201 | 205 | 209 | 213 | 217 | 221 | 194 | 198 | 202 | 206 | 210 | 214 | 218 | 222 |
|   | 225 | 229 | 233 | 237 | 241 | 245 | 249 | 253 | 226 | 230 | 234 | 238 | 242 | 246 | 250 | 254 |
|   | 4 | 8 | 12 | 16 | 20 | 24 | 28 | 32 | 3 | 7 | 11 | 15 | 19 | 23 | 27 | 31 |
|   | 36 | 40 | 44 | 48 | 52 | 56 | 60 | 64 | 35 | 39 | 43 | 47 | 51 | 55 | 59 | 63 |
|   | 68 | 72 | 76 | 80 | 84 | 88 | 92 | 96 | 67 | 71 | 75 | 79 | 83 | 87 | 91 | 95 |
|   | 100 | 104 | 108 | 112 | 116 | 120 | 124 | 128 | 99 | 103 | 107 | 111 | 115 | 119 | 123 | 127 |
|   | 132 | 136 | 140 | 144 | 148 | 152 | 156 | 160 | 131 | 135 | 139 | 143 | 147 | 151 | 155 | 159 |
|   | 164 | 168 | 172 | 176 | 180 | 184 | 188 | 192 | 163 | 167 | 171 | 175 | 179 | 183 | 187 | 191 |
|   | 196 | 200 | 204 | 208 | 212 | 216 | 220 | 224 | 195 | 199 | 203 | 207 | 211 | 215 | 219 | 223 |
|   | 228 | 232 | 236 | 240 | 244 | 248 | 252 | 256 | 227 | 231 | 235 | 239 | 243 | 247 | 251 | 255 |
|   | C |   |   |   |   |   |   |   | D |   |   |   |   |   |   |   |

SCANNING MICROSCOPE AND SPECIMEN IMAGE OBTAINING METHOD IN WHICH ADJACENT DATA OBTAINING POINTS ARE NOT CONSECUTIVELY OBTAINED

CROSS-REFERENCE TO RELATED APPLICATIONS

This application is based upon and claims the benefit of priority from prior Japanese Patent Application No. 2005-010841, filed Jan. 18, 2005, the entire contents of which are incorporated herein by reference.

BACKGROUND OF THE INVENTION

1. Field of the Invention

The present invention relates to a scanning microscope used as a research tool for a biological specimen and to a specimen image obtaining method.

2. Description of the Related Art

Heretofore, a scanning laser microscope has been known as a scanning microscope used as a research tool for a biological specimen wherein laser light is converged on a point on a specimen, and this convergence point is scanned in a two-dimensional direction on the specimen to obtain two-dimensional luminance information on the specimen, for example, as disclosed in Jpn. Pat. Appln. KOKAI Publication No. 10-10436.

Laser light comprising a single beam is used for the scanning laser microscope, and since the laser light has a good convergence property, it is effective in obtaining optical information on a minute point on an XY plane of the specimen. Moreover, because detection light from the specimen is detected by a confocal optical system that detects light through a pinhole located at a position optically conjugate with the convergence point in the specimen, it is possible to eliminate light from out-of-focus positions, and more accurate optical information can be obtained.

Therefore, according to a confocal laser microscope, it is possible to obtain optical information on a point in a three-dimensional space of the specimen. Further, laser light is scanned along the XY plane, an XZ plane, and other two-dimensional planes, and the above-mentioned information for each point can be arranged in accordance with scanned positions, so that optical slice images can be formed. Moreover, a galvanometer mirror is generally used to scan a laser beam. Two galvanometer mirrors are preferably combined so as to scan in XY directions, respectively, so that an imaging region is XY-scanned for each line as a raster scan of a television. In the raster scan, the laser light is sequentially applied to points adjacent in an X direction, and light (fluorescence, reflected light, etc.) from the specimen obtained at that moment is detected by a detector. In this case, a time difference from detection of the fluorescence after application of laser light to arrival at a next point $(X_{n+1}, Y_{n+1})$ is in an order of microsecond.

Meanwhile, the confocal laser microscope is effective in a caged method and the like used for fluorescence observation. Here, the caged method is an observation method wherein a caged indicator and a fluorescence indicator that is sensitive to a calcium ion concentration are injected into a specimen, and stimulating laser light is applied to a certain portion of the specimen, so that a caged radical of the caged indicator is cleaved, substances contained therein are released, and a change over time in the calcium ion concentration at that point is fluorescence-observed by application of observation excitation laser light to the specimen. According to this method, for example, when a caged compound to which calcium ions are bonded is introduced into the specimen, application of UV laser for release of the caged compound at a point $(X_n, Y_n)$ causes the caged compound located at this position to be cleaved, and $Ca^{2+}$ ions retained therein are released. The observed specimen causes a certain reaction to the calcium ions. Fluorescence generated by this reaction is detected by a detector to observe how the specimen reacts to a stimulus of the calcium ions.

BRIEF SUMMARY OF THE INVENTION

The scanning microscope comprises: a light source unit that projects laser light; an optical system that converges and applies the laser light onto a data obtaining point on a specimen; a data obtaining order deciding unit that decides a data obtaining order in which adjacent data obtaining points are not consecutive; a scanning unit that scans the laser light in accordance with the data obtaining order; a detector that detects detection light from the data obtaining point; a storage unit that stores luminance information on the detection light detected by the detector in association with positional information on the data obtaining point; and an image formation unit that forms a two-dimensional image on the basis of the association of the luminance information with the positional information.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 shows an example of an data obtaining order in the confocal laser microscope according to the fourth embodiment of the present invention; and FIG. 10 shows another example of the data obtaining order in the confocal laser microscope according to the fourth embodiment of the present invention.

DETAILED DESCRIPTION OF THE INVENTION

Embodiments of the present invention will hereinafter be described with reference to the drawings.

First Embodiment

Figure 1:
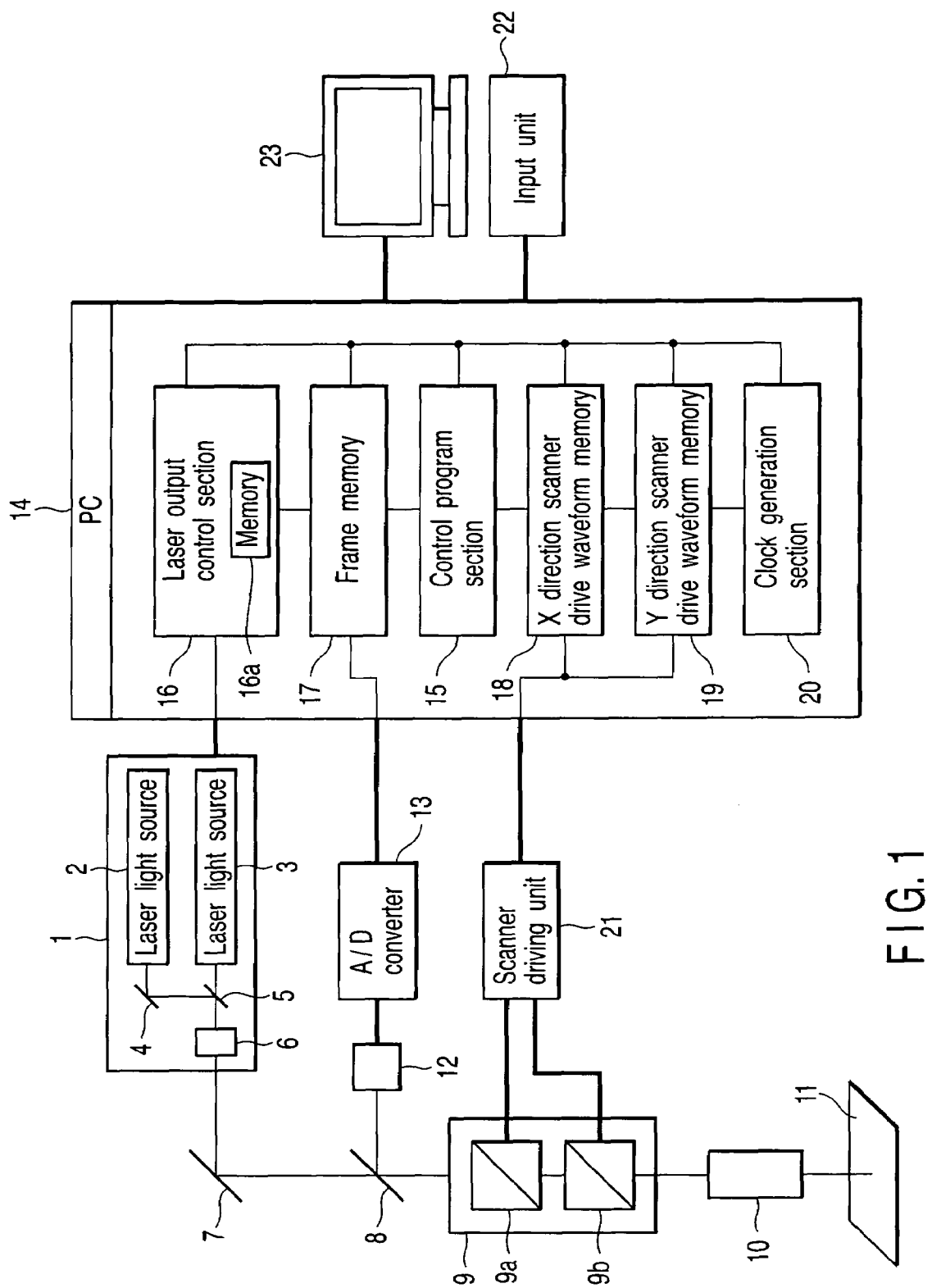
FIG. 1 shows a schematic construction of a confocal laser microscope according to a first embodiment of the present invention.

FIG. 1 shows a schematic construction of a confocal laser microscope according to a first embodiment of the present invention.

As shown in FIG. 1, the confocal laser microscope has a laser unit 1 as a light source unit or light source means for projecting laser light (excitation light), a mirror 7 that bends a path of laser light, a scanning optical unit 9 as a scanning unit or scanning means for two-dimensionally scanning the laser light, an objective lens 10 that converges the laser light on a data obtaining point on a specimen 11, a dichroic mirror 8 that separates the laser light and fluorescence, and a detector 12 as detection means for detecting the fluorescence.

The laser light source unit 1 includes laser light sources 2, 3, a reflecting mirror 4, a dichroic mirror 5, and an acousto-optic tunable filter (AOTF) 6. The laser light sources 2, 3 emit laser light of different wavelengths. The reflecting mirror 4 is located on a path of laser light from the laser light source 2. The dichroic mirror 5 is located on a path of laser light from the laser light source 3 at an intersection with the laser light reflected by the reflecting mirror 4. The dichroic mirror 5 combines the two laser light paths. The dichroic mirror 5 transmits the laser light from the laser light source 3 and reflects the laser light reflected by the reflecting mirror 4. The AOTF 6 is located on a path of laser light combined by the dichroic mirror 5. The AOTF 6 enables control on intensity of the laser light, wavelength components of the laser light, and turning on/off of laser light irradiation.

The reflecting mirror 7 is located on a path of light exiting from the AOTF 6. The dichroic mirror 8 is located on a path of light reflected by the reflecting mirror 7. The dichroic mirror 8 transmits the laser light (excitation light) reflected by the reflecting mirror 7 and reflects detection light (fluorescence) emitted from the specimen 11 described later.

The scanning optical unit 9 is located on a path of light transmitted by the dichroic mirror 8. The scanning optical unit 9 has a Y direction scanner 9a and an X direction scanner 9b that deflect light in two perpendicular directions, and allows the laser light converged on the specimen 11 by the Y direction scanner 9a and the X direction scanner 9b to be applied to any point on a two-dimensional plane.

The objective lens 10 is located on a path of laser light exiting from the scanning optical unit 9. The laser light exiting from the scanning optical unit 9 is converged and applied onto the data obtaining point on the specimen 11 by the objective lens 10. In other words, the objective lens 10 constitutes an optical system as application means for converging and applying the laser light onto the data obtaining point on the specimen 11.

The specimen 11 emits detection light (fluorescence) in response to the application of the laser light (excitation light). The detection light (fluorescence) emitted from the specimen 11 follows backward the optical paths described above to return to the dichroic mirror 8 through the objective lens 10 and the scanning optical unit 9.

The detector 12 is located on a path of detection light selectively reflected by the dichroic mirror 8. The detector 12 comprises, but is not limited to, a photomultiplier, for example. The detector 12 outputs an analog electric signal reflecting luminance of the detection light from the specimen 11.

The confocal laser microscope further has an A/D converter 13 as signal processing means, a personal computer (PC) 14 as control means, a scanner driving unit 21 as driving means for driving the Y direction scanner 9a and the X direction scanner 9b, an input unit 22 as information input means, and a monitor 23 as display means.

The input unit 22 comprises, but is not limited to, a keyboard, for example. Alternatively, the input unit 22 may also comprise a pointing device such as a mouse and a graphical user interface (GUI). The monitor 23 comprises, but is not limited to, a CRT, for example.

The personal computer (PC) 14 is connected to the detector 12 through the A/D converter 13. The A/D converter 13 converts the analog electric signal from the detector 12 into a digital signal to output it to the PC 14.

The PC 14 has a control program section 15, a laser output control section 16, a frame memory 17, an X direction scanner drive waveform memory 18, a Y direction scanner drive waveform memory 19 and a clock generation section 20.

The frame memory 17 stores luminance data detected by the detector 12 and converted into the digital signal through the A/D converter 13 in association with point coordinates (positional information on the data obtaining point) within an imaging region. The frame memory 17 constitutes storage means for preserving the luminance information on the detection light in association with the positional information on the data obtaining point.

Figure 2:
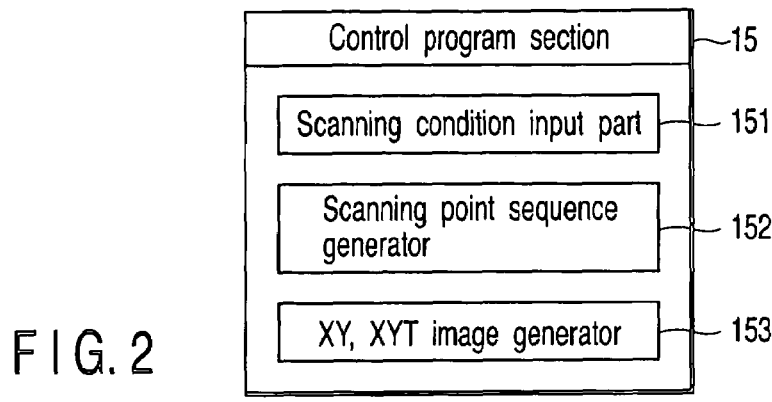
FIG. 2 shows a schematic construction of a control program section used in the first embodiment.

As shown in FIG. 2, the control program section 15 has a scanning condition input part 151, a scanning point sequence generator 152, and an XY, XYT image generator 153. Scanning conditions, such as an XY scan size, a sampling speed, and data obtaining time per point in the imaging region, are input to the scanning condition input part 151 from the input unit 22. The scanning point sequence generator 152 creates a random scanning point sequence in which data is not consecutively obtained regarding two adjacent points in the imaging region. The scanning point sequence generator 152 constitutes data obtaining order deciding means for deciding a data obtaining order in which adjacent data obtaining points are not consecutive. The random scanning point sequence is created by use of, for example, random numbers. And the random scanning point sequence is then checked whether it includes sequential two points that are spatially adjacent. In such a case, the scanning point sequence generator 152 carries out a proper process, such as a process that replaces one of the sequential two points with another point. The XY, XYT image generator 153 generates image data on the basis of the association of the luminance data written into the frame memory 17 with the point coordinates (positional information on the data obtaining point) within the imaging region. The XY, XYT image generator 153 constitutes image formation means for forming a two-dimensional image on the basis of the association of the luminance information on the detection light with the positional information on the data obtaining point.

The laser output control section 16 controls output of laser light of the laser light source unit 1 in accordance with the data obtaining time per point set in the scanning condition input part 151.

The X direction scanner drive waveform memory 18 and the Y direction scanner drive waveform memory 19 store drive waveform data (waveform DAC data provided to a D/A converter of the scanner driving unit 21) to drive the X direction scanner 9b and the Y direction scanner 9a converted from the random scanning point sequence generated by the scanning point sequence generator 152.

The scanner driving unit 21 is connected to the X direction scanner drive waveform memory 18 and the Y direction scanner drive waveform memory 19. The scanner driving unit 21 drives the Y direction scanner 9a and the X direction scanner 9b in accordance with waveform data (waveform DAC data) from the X direction scanner drive waveform memory 18 and the Y direction scanner drive waveform memory 19 synchronously read from a clock pulse of the clock generation section 20.

The clock generation section 20 generates the clock pulse that decides operation timing of the control program section 15, the laser output control section 16, the frame memory 17, the X direction scanner drive waveform memory 18, and the Y direction scanner drive waveform memory 19.

Next, an operation of the first embodiment will be described.

First, the scanning conditions are input from the input unit 22 to the scanning condition input part 151 of the PC 14. The scanning conditions to be input include, for example, the XY scan size to decide the imaging region (e.g., 512×512 points), the sampling speed to decide sampling intervals of the detection signal for the A/D converter, and the data obtaining time per point in the imaging region. Then, the scanning point sequence generator 152 creates the random scanning point sequence in which data is not consecutively obtained regarding two adjacent points in the imaging region, so that the data obtaining order is decided in which any sequential two of data obtaining points never adjoin each other. Moreover, a sampling number per point is calculated in accordance with the sampling speed and the data obtaining time per point. In this first embodiment, the sampling number per point is set to one.

Next, the random scanning point sequence (coordinate data) generated by the scanning point sequence generator 152 is converted into drive waveform data (waveform DAC data) to drive the X direction scanner 9b and the Y direction scanner 9a, and then stored in the X direction scanner drive waveform memory 18 and the Y direction scanner drive waveform memory 19.

Figure 3A:
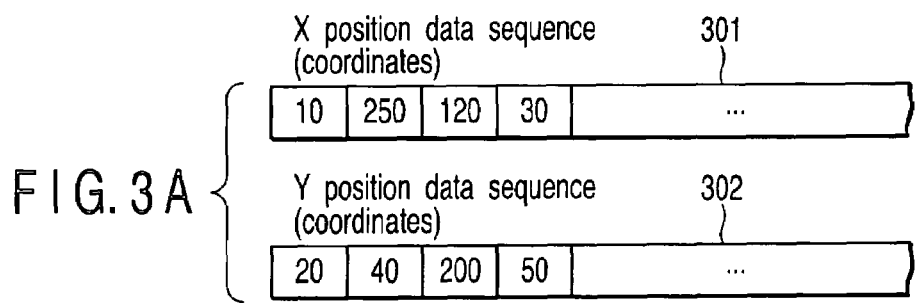
FIG. 3A shows an X position data sequence and a Y position data sequence.
Figure 3B:
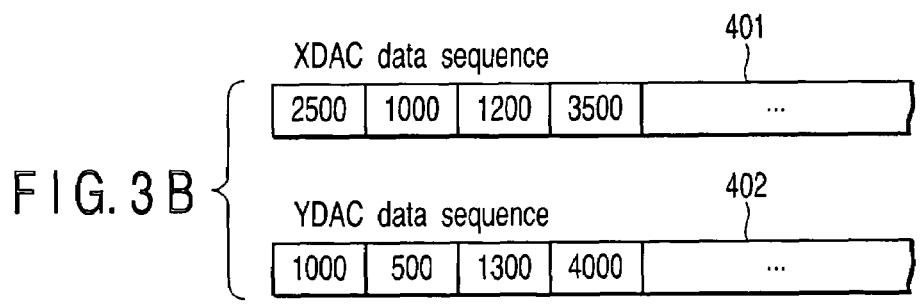
FIG. 3B shows a XDAC data sequence and a YDAC data sequence, in the first embodiment.

The random scanning point sequence is provided as coordinate data on 512×512 points including an X position data sequence 301 of (10), (250), (120), . . . and a Y position data sequence 302 of (20), (40), (200), . . . , for example, as shown in FIG. 3A. These coordinate data are converted into a XDAC data sequence 401 of (2500), (1000), . . . and a YDAC data sequence 402 of (1000), (500), . . . , as shown in FIG. 3B. Further, DAC data of the XDAC data sequence 401 and the YDAC data sequence 402 are stored in the X direction scanner drive waveform memory 18 and the Y direction scanner drive waveform memory 19.

The drive waveform data of the X direction scanner drive waveform memory 18 and the Y direction scanner drive waveform memory 19 are read by the scanner driving unit 21 synchronously with the clock pulse of the clock generation section 20, and the scanner driving unit 21 drives the Y direction scanner 9a and the X direction scanner 9b. At the same time, the laser light source unit 1 projects laser light under the instruction of the laser output control section 16. The laser light is defected by the Y direction scanner 9a and the X direction scanner 9b, and applied to each data obtaining point on the specimen 11 through the objective lens 10 in order.

In response to the application of the laser light, detection light (fluorescence) is emitted from each data obtaining point on the specimen 11. The detection light (fluorescence) enters the dichroic mirror 8 through the objective lens 10 and the scanning optical unit 9, is reflected by the dichroic mirror 8, and detected by the detector 12. The detector 12 outputs an analog signal reflecting luminance of the detection light. The analog signal output from the detector 12 is converted into a digital signal by the A/D converter 13, and written into the frame memory 17. The luminance data on each point within the imaging region obtained by the detector 12 is written into the frame memory 17 in association with random scanning points (the X position data sequence 301 and the Y position data sequence 302 shown in FIG. 3A) generated by the scanning point sequence generator 152.

Furthermore, the XY, XYT image generator 153 generates an XY image data on the basis of the association of the luminance data written in the frame memory 17 with point coordinates within the imaging region. An image corresponding to the XY image data is displayed on the monitor 23.

In a conventional raster scan, data is obtained with regard to a point (Xn, Yn), immediately after which data is obtained with regard to an adjacent point (Xn+1, Yn). In an observation according to the caged method, for example, an influence of the calcium ions released from the point (Xn, Yn) is not limited to the point (Xn, Yn), but can be exerted to its periphery (e.g., a next point (Xn+1, Yn)). Thus, the data for the point (Xn+1, Yn) might incorporate the influence of the reaction behavior to the stimulus at the previous point (Xn, Yn). Also in a fluorescent observation without stimulation, in case that fluorescence has a long life of a microsecond order, data for the point (Xn+1, Yn) might be influenced by the previous point (Xn, Yn).

On the contrary, in the present embodiment, the random scanning point sequence in which data is not consecutively obtained regarding two adjacent points in the imaging region (e.g., 512×512 points) is created to decide the data obtaining order, drive signals for the Y direction scanner 9a and the X direction scanner 9b are generated in accordance with the decided obtaining order, point scanning is performed in accordance with the drive signals, the detection light from each data obtaining point is detected to obtain the luminance data, the obtained luminance data on each point is stored in the frame memory 17 in association with the random scanning point sequence, and the luminance data on all the points are obtained to complete a two-dimensional image. Thus, the data obtained from each point does not include data consecutively obtained from two adjacent points, and is not influenced by light at other points. That is, it is ensured that mutual influences of points in obtaining data are eliminated. Therefore, luminance at individual points is correctly detected without being influenced by other points.

It is to be noted that the laser light is continuously projected while the data obtaining point is being moved in the embodiment described above. However, the AOTF 6 may be controlled synchronously with operations of the Y direction scanner 9a and the X direction scanner 9b, and the application of the laser light may be stopped while the data obtaining point is being moved to a next data obtaining point. This can eliminate all the influences exerted by the laser light during the movement of the data obtaining point. In addition, the imaging region may be limited to a region where the specimen exists in stead of a fixed rectangular shape.

Second Embodiment

A schematic construction of a confocal laser microscope according to a second embodiment is similar to that in FIG. 1, and FIG. 1 is therefore used.

In the first embodiment, the data obtaining time per point is set to a time corresponding to one sampling, so that an XY image of a specimen 11 is obtained a point. However, in this second embodiment, XYT images, which are a stack (bundle) of time sequential XY images, are obtained by performing a plurality of samplings during the data obtaining time per point.

A sampling number per point calculated in accordance with a sampling speed and the data obtaining time per point is set to a plurality of samplings, for example, 50 samplings. Moreover, 50 frame memories 17 are prepared to correspond to the sampling number per point.

Figure 4A:
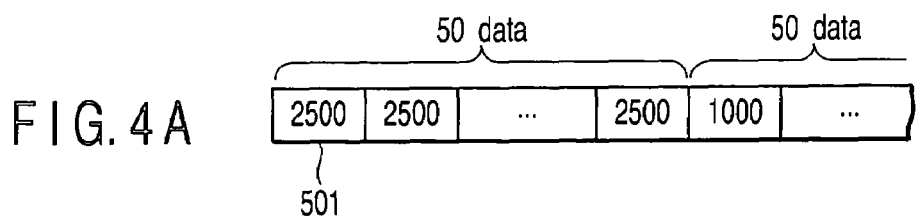
FIGS. 4A and 4B show a XDAC data sequence and a YDAC data sequence in a second embodiment of the present invention, respectively.
Figure 4B:
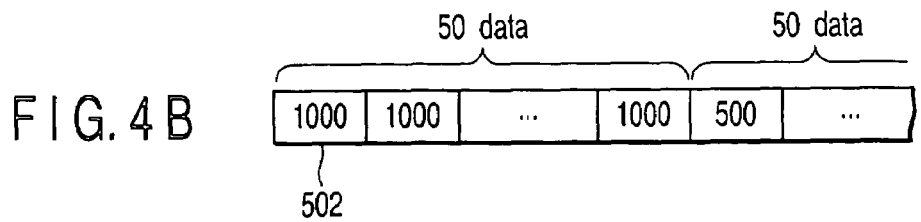

A random scanning point sequence generated by the scanning point sequence generator 152 includes, for example, an X position data sequence 301 and a Y position data sequence 302 shown in FIG. 3A described above, which are provided as coordinate data on an imaging region. Regarding drive waveform data (waveform DAC data) converted by the X position data sequence 301 and the Y position data sequence 302, XDAC data (2500) corresponding to 50 data is generated for initial X position data (10) shown in FIG. 3A, and similarly, YDAC data (1000) corresponding to 50 data is generated for initial Y position data (20). Subsequently, XDAC data and YDAC data each corresponding to 50 data are similarly generated for XY position data at each data obtaining point. FIG. 4A and FIG. 4B show an XDAC data sequence 501 and a YDAC data sequence 502 thus generated, respectively.

The XDAC data sequence 501 and the YDAC data sequence 502 are stored in an X direction scanner drive waveform memory 18 and a Y direction scanner drive waveform memory 19, respectively.

The drive waveform data in the X direction scanner drive waveform memory 18 and the Y direction scanner drive waveform memory 19 are read by the scanner driving unit 21 synchronously with a clock pulse of the clock generation section 20, and the scanner driving unit 21 drives the Y direction scanner 9a and the X direction scanner 9b.

In this state, laser light projected from the laser light source unit 1 is deflected by the Y direction scanner 9a and the X direction scanner 9b, and applied to each data obtaining point on the specimen 11 through the objective lens 10. In response to the application of the laser light, detection light (fluorescence) is emitted from each data obtaining point on the specimen 11. The detection light (fluorescence) is detected by the detector 12. The detector 12 outputs an analog signal reflecting luminance of the detection light. The analog signal output from the detector 12 is converted into a digital signal by the A/D converter 13, and written into a frame memory 17.

Figure 5:
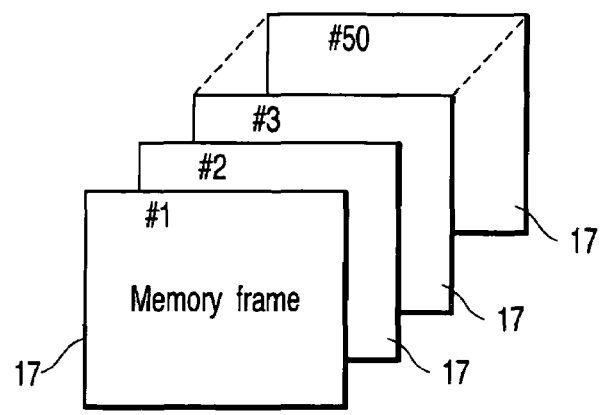
FIG. 5 shows a schematic construction of a frame memory used in the second embodiment.

In this case, luminance data corresponding to first XDAC data of the XDAC data sequence 501 and first YDAC data of the YDAC data sequence 502 is written into a frame memory 17 of #1 associated with a random scanning point (the X position data sequence 301 and the Y position data sequence 302 shown in FIG. 3A) generated by the scanning point sequence generator 152. Moreover, luminance data corresponding to second XDAC data of the XDAC data sequence 501 and second YDAC data of the YDAC data sequence 502 is written into a frame memory 17 of #2 associated with the random scanning point generated by the scanning point sequence generator 152. Subsequently, luminance data corresponding to third to fiftieth XDAC data of the XDAC data sequence 501 and third to fiftieth YDAC data of the YDAC data sequence 502 are similarly written into frame memories 17 of #3 to #50 in relevant ranks. This operation is repeated for all the luminance data obtained in conformity with the XDAC data of the XDAC data sequence 501 and the YDAC data of the YDAC data sequence 502 corresponding to the random scanning point, and the luminance data are written into the frame memories 17 of #1 to #50 as shown in FIG. 5.

Furthermore, the XY, XYT image generator 153 generates XYT image data on the basis of the association of the luminance data written into the frame memories 17 of #1 to #50 with data obtaining point coordinates within the imaging region. Images corresponding to the XY image data are individually displayed on the monitor 23.

In the present embodiment, data is repeatedly obtained (sampled) a plurality of times at predetermined time intervals for each data obtaining point randomly set. Out of luminance data (t=T1, T2, . . . , Tn) (n=50) to be obtained at each point, those detected at the same rank are individually written into the frame memories 17 of #1 to #50. Thus, detection data at each point is not influenced by other points, and it is possible to observe a dynamic change of a reaction behavior to a stimulus of the specimen 11 by the XYT images generated in the XY, XYT image generator 153 on the basis of the luminance data written into the frame memories 17.

Third Embodiment

A schematic construction of a confocal laser microscope according to a third embodiment is similar to that in FIG. 1, and FIG. 1 is therefore used.

In the third embodiment, a plurality of samplings are performed during the data obtaining time per point, and laser conditions such as intensity of laser light, wavelength components of the laser light, and turning on/off of laser light irradiation are set in conformity with the clocks per point.

A sampling number per point calculated in accordance with a sampling speed and a data obtaining time per point is set to, for example, 10 samplings.

A random scanning point sequence generated by the scanning point sequence generator 152 includes, for example, an X position data sequence 301 and a Y position data sequence 302 shown in FIG. 3A described above, which are provided as coordinate data in an imaging region. In a procedure similar to that described in the second embodiment, drive waveform data (X(Y) DAC data) A1, A2, . . . , A10 corresponding to ten data are generated for initial positional data of the X position data sequence 301 and the Y position data sequence 302. Subsequently, in the same manner, X(Y) DAC data B1, B2, . . . , C1, C2, . . . each corresponding to ten data are generated for the following positional data. An upper step in FIG. 6 shows an X(Y) DAC data 601 thus generated.

Figure 6:
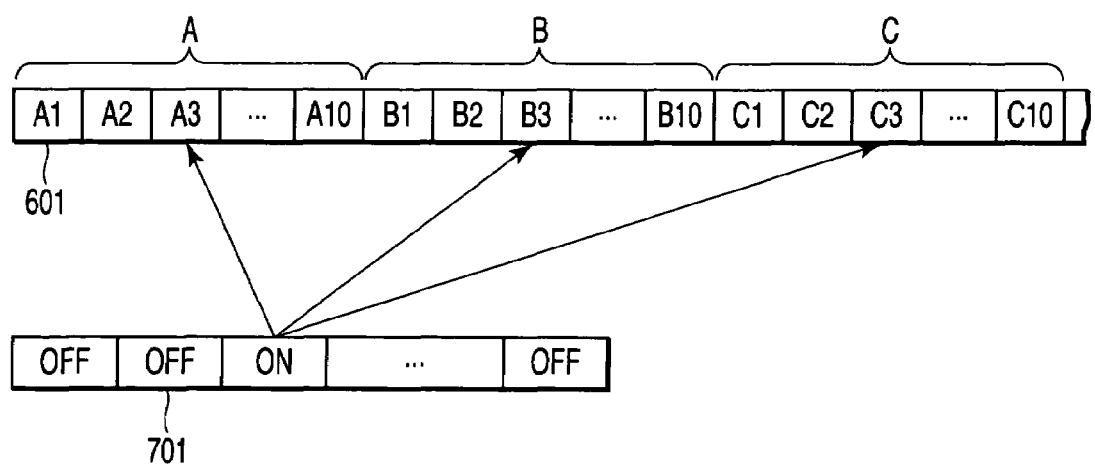
FIG. 6 shows a laser setting data sequence according to a third embodiment of the present invention.

Furthermore, a laser setting data sequence 701 in which the laser conditions are written as shown in a lower step of FIG. 6 is generated in conformity with X(Y) DAC data A1, A2, . . . , B1, B2, . . . , C1, C2, . . . each corresponding to ten data. In laser setting data, on data ON concerning laser light irradiation is set only for the X(Y) DAC data A3, B3, C3, . . . , and off data OFF concerning the laser light irradiation is set for other X(Y) DAC data.

The laser setting data sequence 701 is stored in the memory 16a of the laser output control section 16. The laser output control section 16 reads the laser setting data sequence 701 stored in the memory 16a synchronously with the sampling timing in obtaining data, and the turning on/off of the laser light irradiation is controlled by the AOTF 6.

In this construction, a data obtaining point on the specimen 11 is set in accordance with the X(Y) DAC data A1, A2, . . . , B1, B2, . . . , C1, C2, . . . of the X(Y) DAC data sequence 601 read synchronously with a clock pulse of the clock generation section 20. At the same time, the turning on/off of the laser light irradiation is controlled on the basis of the laser setting data of the laser setting data sequence 701. In this case, since the on data ON of laser light irradiation is set in the laser setting data sequence 701 only for A3, B3, C3, . . . out of the X(Y) DAC data A, B, C, . . . each corresponding to ten data, the AOTF 6 is turned on only with these timings, so that the illumination light is applied to the sample.

In the present embodiment, light from each data obtaining point is detected a plurality of times at predetermined time intervals, and different laser conditions can be set in association with a detection timing of each of the detections. Here, for a plurality of luminance data (t=T1, T2, . . . , Tn) (n=10) obtained by a plurality of data obtaining (samplings) at a data obtaining point, the laser light irradiation is turned on only for t=T3 (A3, B3, C3, . . . ), and the laser light irradiation is turned off for others including t=T1, T2, T4, . . . , Tn, so that it is possible to observe states of the specimen 11 including states before stimulation, and to observe dynamic behaviors of the specimen 11 at a point of stimulation and after the stimulation is stopped.

It is to be noted that a data condition set when obtaining data a plurality of times at the data obtaining point is not limited to the turning on/off of the laser light irradiation, and one or both of the intensity and the wavelength components of the laser light can be varied and set. In an observation of a fluorescence specimen multi-dyed, for example, laser light having an excitation wavelength corresponding to each of fluorescence dyes may be sequentially applied to the specimen.

Fourth Embodiment

Figure 7:
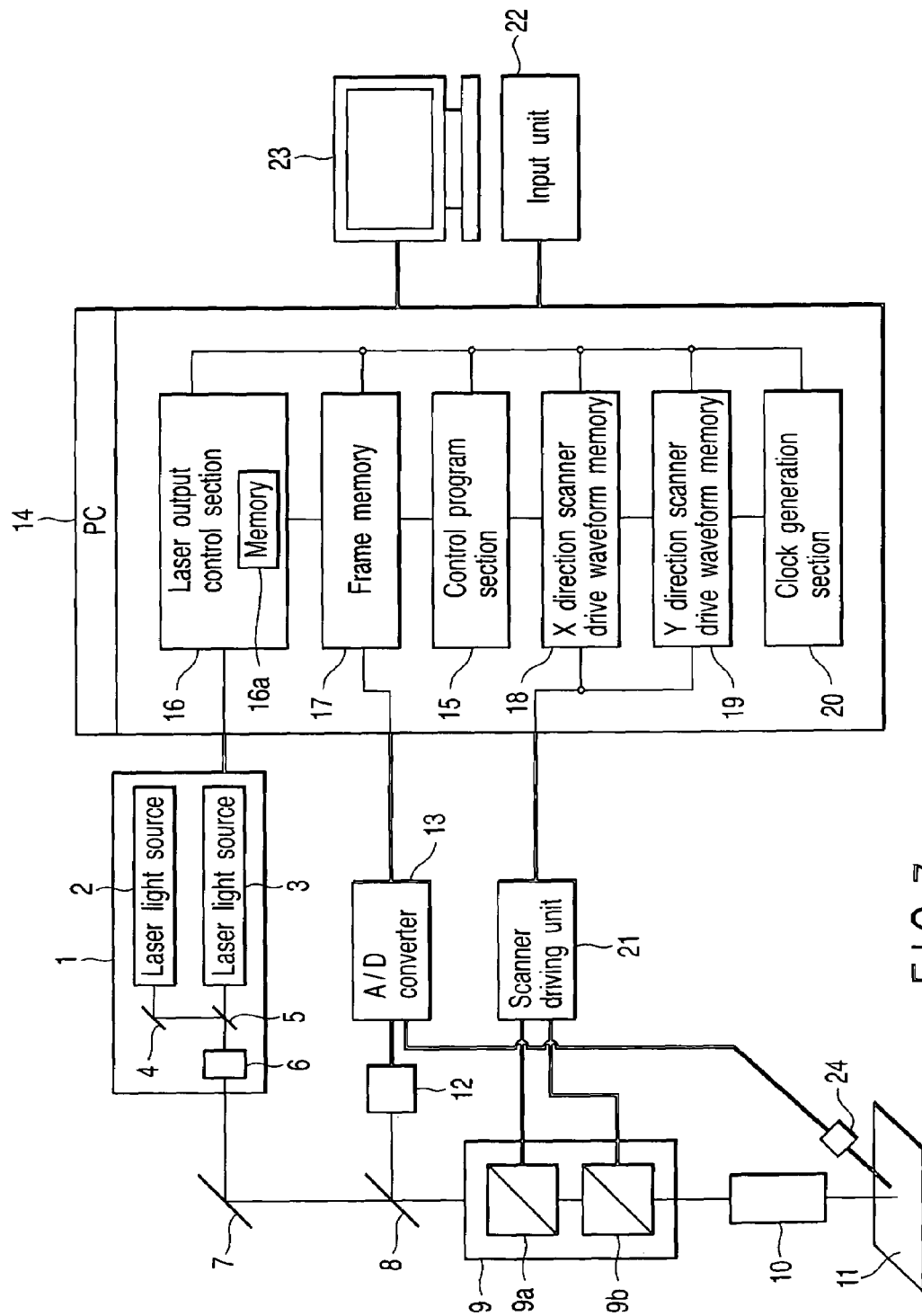
FIG. 7 shows a schematic construction of a confocal laser microscope according to a fourth embodiment of the present invention.

FIG. 7 shows a schematic construction of a confocal laser microscope according to a fourth embodiment of the present invention. In FIG. 7, members indicated by the same reference numerals as those of members shown in FIG. 1 are the same, and will not be described in detail.

The confocal laser microscope of the present embodiment further has, as shown in FIG. 7, a current detector 24 as current detection means for detecting a current value from the specimen 11, in addition to an apparatus construction of FIG. 1. The current detector 24 outputs an analog electric signal reflecting a detected current value.

The analog signal of the current value output from the current detector 24 is input to the A/D converter 13 and converted into a digital signal, in the same manner as luminance of detection light from the detector 12. The current value data is written into the frame memory 17 as luminance information. That is, the current value is obtained with the same timing as sampling timing of fluorescence detection. The current value data is written into the frame memory 17 in association with a random scanning point (an X position data sequence 301 and a Y position data sequence 302 shown in FIG. 3A) generated by the scanning point sequence generator 152.

Furthermore, the XY, XYT image generator 153 generates an XY image data on the basis of the association of the current data written into the frame memory 17 with point coordinates within an imaging region. An image corresponding to the XY image data is displayed on the monitor 23.

In the present embodiment, the current value can be measured in such a manner as to eliminate an influence of the preceding laser irradiation. Therefore, it is possible to accurately visualize an electric reaction of the specimen 11 when laser light is applied to each data obtaining point of the specimen 11. The present embodiment is carried out in combination with any one of the first through third embodiments.

Application of the Fourth Embodiment

Figure 8:
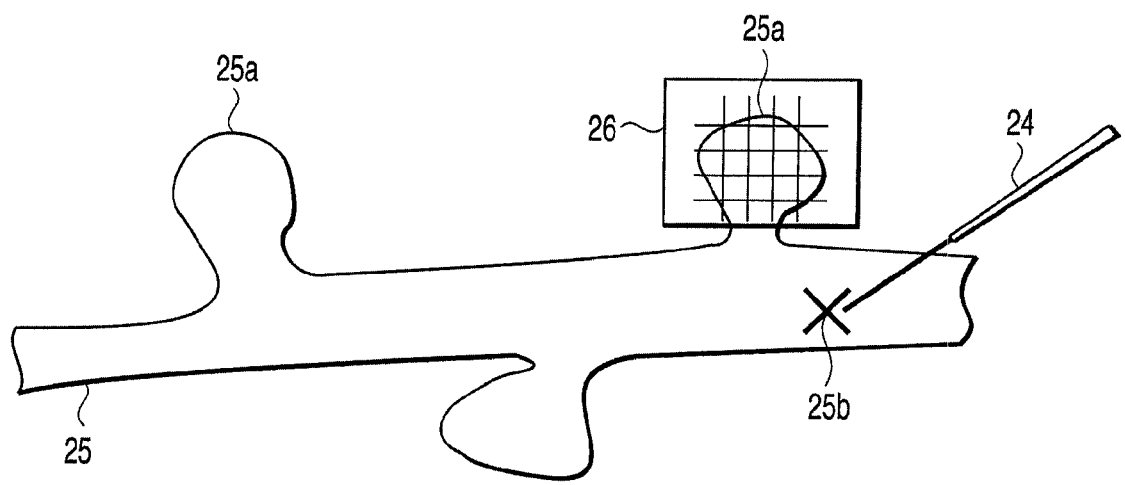
FIG. 8 shows an application of a current measurement by the confocal laser microscope of the fourth embodiment.

As shown in FIG. 8, stimulus light is applied to an area 26 including a spine 25a of a nerve cell 25 in a random scan method, and a reaction of the nerve cell 25 to this stimulus is measured by the current detector 24 inserted into a part 25b.

The measurement of the current value may be performed for a plurality of parts. In that case, the current detectors 24 are inserted into the respective measurement parts.

Fifth Embodiment

A data obtaining order in which adjacent data obtaining points are not consecutive is decided at random in the first embodiment. On the contrary, in the present embodiment, a data obtaining order in which adjacent data obtaining points are not consecutive is regularly decided.

A schematic construction of a confocal laser microscope according to a fifth embodiment is similar to that in FIG. 1, and FIG. 1 is therefore used.

In the fifth embodiment, the scanning point sequence generator 152 generates a scanning point sequence of an irradiation order shown in, for example, FIG. 9 or 10. The XY, XYT image generator 153 generates, like the first embodiment, an image data on the basis of the association of the obtained luminance data and the scanning point coordinates.

In an example of FIG. 9, a scanning region is divided into eight regions A to H of the same size. Then, upper left points of the divided regions are irradiated in order of ACEGBDFH. After a round, next points are similarly irradiated in an X line direction in order of ACEGBDFH. After completing the irradiation for a line, a second line in each region is irradiated in the same manner. That is, the laser light is applied to the regions A to H in a fixed order in accordance with the same rule. FIG. 9 shows an irradiation order in a scanning region of 16×16 pixels. Numbers in frames indicate the irradiation order. In this example, a point next to a point irradiated first is irradiated ninth, so that a time interval of the laser applications to the adjacent points is a data obtaining time corresponding to eight pixels.

In an example of FIG. 10, a scanning region is divided into four regions A to D of the same size. Then, the divided regions are irradiated in order of ABDC in the same manner as described above. In this example, a point next to a point irradiated first is irradiated fifth, so that a time interval of the laser applications to the adjacent points is an obtaining time corresponding to four pixels. Moreover, if the irradiation is implemented in order of ABCD, moving distances from B to C and from D to A will be larger than other moving distances, but in the present embodiment, the irradiation is implemented in order of ABDC, so that the inter-region moving distances can be substantially uniform. This is thus advantageous in enhancing safety of scanning in discontinuous scanning on a pixel-to-pixel basis.

In addition to FIG. 9 and FIG. 10, the divided regions may be suitably set in an X direction or Y direction to adjust irradiation time intervals of adjacent irradiation points. Moreover, the irradiation order may also be suitably changed; for example, irradiation may be implemented in order in the Y direction.

Such an irradiation order (point sequence) may be stored in the memory in advance and called in use, or may be decided every time by use of a computation formula to decide a sequence. This scanning manner may be used in combination with any one of the aforementioned second through fourth embodiments.

In addition, the present invention is not limited to the embodiments described above, and various modifications may be made in an implementation stage without changing the spirit of the present invention.

For example, laser scanning may be implemented in such a manner that an image for a frame is first obtained (both an ordinary XY scan or a random scan of the present invention will do) to detect a position where a specimen exists or to specify the position on a monitor, and only for the position where the specimen exists, a data obtaining order in which adjacent data obtaining points are not consecutive is decided. In this way, image obtaining time is significantly reduced because positions where the specimen does not exist are not scanned. Further, a plane of which an image is to be obtained may be an XZ plane or a plane inclined with respect to a laser light axis, instead of an XY plane. In this case, an optical element such as a deformable mirror may be provided in the optical axis to move a convergent point in a Z direction at high speed.

Furthermore, the embodiments described above include inventions at various stages, and suitable combinations of disclosed constitutional requirements allow various inventions to be extracted. For example, when the advantages described in the embodiments can be obtained even if some of all the constitutional requirements shown in the embodiments are eliminated, a construction in which those constitutional requirements are eliminated can be extracted as an invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A scanning microscope comprising:
   a light source unit that projects laser light;
   an optical system that converges and applies the laser light individually onto data obtaining points on a continuous biological specimen;
   a data obtaining order deciding unit that decides a data obtaining order such that spatially adjacent data obtaining points are not consecutive in the data obtaining order;
   a scanning unit that optically scans the laser light in a two-dimensional plane of the specimen in accordance with the data obtaining order;
   a detector that detects detection light from the data obtaining points, respectively;
   a storage unit that stores luminance information on the detection light detected by the detector in association with positional information on the data obtaining points, respectively; and
   an image formation unit that forms a two-dimensional image based on the stored associated luminance and positional information,
   wherein the data obtaining order deciding unit is configured to randomly decide the data obtaining order and check whether the data obtaining order includes sequential two points that are spatially adjacent, and wherein when it is determined that the data obtaining order includes the sequential two points that are spatially adjacent, the data obtaining order deciding unit replaces one of the sequential two points with another point.

2. The scanning microscope according to claim 1, wherein after the detector detects the detection light from a data obtaining point a plurality of times at predetermined time intervals, the scanning unit moves the laser light to a next data obtaining point, and the image formation unit forms a two-dimensional image for each detection rank by associating each of the luminance information on the detection light at a same rank in the luminance information on the detection light from the data obtaining points detected by the detector with the positional information on the data obtaining points.

3. The scanning microscope according to claim 1, wherein the detector detects a current value generated in the specimen synchronously with the detection of the detection light from a data obtaining point when the laser light is applied to the data obtaining point.

4. The scanning microscope according to claim 1, further comprising a laser light control unit that controls at least one of a wavelength and an intensity of the laser light projected from the light source unit, wherein after the detector detects the detection light from a data obtaining point a plurality of times at predetermined time intervals, the scanning unit moves the laser light to a next data obtaining point, and wherein the laser light control unit changes an irradiation condition of the laser light in association with a detection order at each data obtaining point.

5. The scanning microscope according to claim 4, wherein the irradiation condition of the laser light is at least one of turning on/off of laser light irradiation, intensity of the laser light, and wavelength components of the laser light.

6. The scanning microscope according to claim 1, wherein the data obtaining order deciding unit is also configured to regularly decide the data obtaining order.

7. The scanning microscope according to claim 6, wherein the data obtaining order deciding unit is configured to divide a scanning region into plural regions, and decide an order in which the laser light is regularly applied to the plural regions in accordance with a same rule.

8. A scanning microscope comprising:
   light source means for projecting laser light;
   application means for converging and applying the laser light individually onto data obtaining points on a continuous biological specimen;
   data obtaining order deciding means for deciding a data obtaining order such that spatially adjacent data obtaining points are not consecutive in the data obtaining order;
   scanning means for optically scanning the laser light in a two-dimensional plane of the specimen in accordance with the data obtaining order;
   detection means for detecting detection light from the data obtaining points, respectively;
   storage means for preserving luminance information on the detection light detected by the detection means in association with positional information on the data obtaining points, respectively; and
   image formation means for forming a two-dimensional image based on the stored associated luminance and positional information,
   wherein the data obtaining order deciding means is configured to randomly decide the data obtaining order and check whether the data obtaining order includes sequential two points that are spatially adjacent, and wherein when it is determined that the data obtaining order includes the sequential two points that are spatially adjacent, the data obtaining order deciding means replaces one of the sequential two points with another point.

9. The scanning microscope according to claim 8, wherein after the detection means detects the detection light from a data obtaining point a plurality of times at predetermined time intervals, the scanning means moves the laser light to a next data obtaining point, and the image formation means forms a two-dimensional image for each detection rank by associating each of the luminance information on the detection light at a same rank in the luminance information on the detection light from the data obtaining points detected by the detection means with the positional information on the data obtaining points.

10. The scanning microscope according to claim 8, wherein the detection means detects a current value generated in the specimen synchronously with the detection of the detection light from a data obtaining point when the laser light is applied to the data obtaining point.

11. The scanning microscope according to claim 8, further comprising laser light control means for controlling at least one of a wavelength and an intensity of the laser light projected from the light source means, wherein after the detection means detects the detection light from a data obtaining point a plurality of times at predetermined time intervals, the scanning means moves the laser light to a next data obtaining point, and wherein the laser light control means changes an irradiation condition of the laser light in association with a detection order at each data obtaining point.

12. The scanning microscope according to claim 11, wherein the irradiation condition of the laser light is at least one of turning on/off of laser light irradiation, intensity of the laser light and wavelength components thereof.

13. The scanning microscope according to claim 8, wherein the data obtaining order deciding means is also configured to regularly decide the data obtaining order.

14. The scanning microscope according to claim 13, wherein the data obtaining order deciding means is configured to divide a scanning region into plural regions, and decide an order in which the laser light is regularly applied to the plural regions in accordance with a same rule.

15. A specimen image obtaining method comprising:
converging and applying laser light individually onto data obtaining points on a continuous biological specimen;
deciding a data obtaining order in which spatially adjacent data obtaining points are not consecutive;
optically scanning the laser light in a two-dimensional plane of the specimen in accordance with the data obtaining order;
detecting detection light from the data obtaining points, respectively;
storing luminance information on the detection light detected from the data obtaining points in association with positional information on the data obtaining points, respectively; and
forming a two-dimensional image based on the stored associated luminance and positional information,
wherein the data obtaining order is decided randomly and it is checked whether the data obtaining order includes sequential two points that are spatially adjacent, and wherein when it is determined that the data obtaining order includes the sequential two points that are spatially adjacent, one of the sequential two points is replaced with another point.

16. A scanning microscope comprising:
a light source unit that projects laser light;
an optical system that converges and applies the laser light onto data obtaining points on a continuous biological specimen which contains a compound that causes a photochemical reaction;
a data obtaining order deciding unit that decides a data obtaining order of the data obtaining points such that a second data obtaining point, where data is obtained time-sequentially next to a first data obtaining point, is located away from the first data obtaining point by a distance such that the second data obtaining point is not affected by the photochemical reaction caused by the application of the laser light to the first data obtaining point;
a scanning unit that scans the laser light optically on a two-dimensional plane of the specimen in accordance with the data obtaining order;
a detector that detects detection light from the data obtaining points;
a storage unit that stores luminance information on the detection light detected by the detector in association with positional information on the data obtaining points; and
an image formation unit that forms a two-dimensional image based on the association of the luminance information with the positional information,
wherein the data obtaining order deciding unit is configured to randomly decide the data obtaining order and check whether the data obtaining order includes sequential two points that are spatially adjacent, and wherein when it is determined that the data obtaining order includes the sequential two points that are spatially adjacent, the data obtaining order deciding unit replaces one of the sequential two points with another point.

* * * * *